United States Patent
Vinup et al.

(10) Patent No.: US 7,363,089 B2
(45) Date of Patent: Apr. 22, 2008

(54) METHOD OF USE OF IMPLANTABLE PERCUTANEOUS STIMULATION LEAD

(75) Inventors: Dan K. Vinup, Lakeville, MN (US); Jane L. Kohnen, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 198 days.

(21) Appl. No.: 11/370,742

(22) Filed: Mar. 7, 2006

(65) Prior Publication Data

US 2006/0149344 A1    Jul. 6, 2006

Related U.S. Application Data

(63) Continuation of application No. 09/957,217, filed on Sep. 20, 2001, now Pat. No. 7,072,719.

(51) Int. Cl.
*A61N 1/05* (2006.01)
(52) U.S. Cl. .................... 607/116; 607/117; 128/898; 600/373
(58) Field of Classification Search ............. 607/116, 607/117, 122; 606/108; 128/898; 600/378, 600/393
See application file for complete search history.

(56) References Cited

U.S. PATENT DOCUMENTS

| | | |
|---|---|---|
| 4,044,774 A | 8/1977 | Corbin et al. |
| 4,141,365 A | 2/1979 | Fischell et al. |
| 4,270,549 A | 6/1981 | Heilman |
| 4,271,847 A * | 6/1981 | Stokes .................. 607/122 |
| 4,285,347 A | 8/1981 | Hess |
| 4,332,259 A | 6/1982 | McCorkle, Jr. |
| 4,601,713 A | 7/1986 | Fuqua |
| 5,107,856 A | 4/1992 | Kristiansen et al. |
| 5,255,691 A | 10/1993 | Otten |
| 5,417,719 A | 5/1995 | Hull et al. |
| 5,443,065 A | 8/1995 | Berghoff et al. |
| 5,618,287 A | 4/1997 | Fogarty et al. |
| 5,669,882 A | 9/1997 | Pyles |
| 5,679,026 A | 10/1997 | Fain et al. |

(Continued)

FOREIGN PATENT DOCUMENTS

EP    1048270    11/2000

(Continued)

OTHER PUBLICATIONS

Brochure, "Implantable Neurostimulation System", *Medtronic, Inc.*, 6 pgs. (1998).

(Continued)

*Primary Examiner*—Kennedy J. Schaetzle
(74) *Attorney, Agent, or Firm*—Stephen W. Bauer; Rick L. Franzen

(57) ABSTRACT

A percutaneous neurological stimulation lead has at least a first lead body and a second lead body that interlock during implantation using interlocking elements. The first lead body has at least one first detail on the first lead body distal end that is configured to engage at least one second detail on the second lead body distal end that is complimentary to the first detail to mechanically couple the first lead body to the second lead body. Many embodiments of the implantable neurological stimulation lead with interlocking elements and its methods of operation are possible.

3 Claims, 5 Drawing Sheets

U.S. PATENT DOCUMENTS

| | | |
|---|---|---|
| 5,707,399 A | 1/1998 | Killander et al. |
| 5,733,322 A | 3/1998 | Starkebaum |
| 5,762,629 A | 6/1998 | Kambin |
| 5,782,892 A | 7/1998 | Castle et al. |
| 5,902,331 A | 5/1999 | Bonner et al. |
| 6,205,361 B1 | 3/2001 | Kuzma et al. |
| 6,249,707 B1 | 6/2001 | Kohnen et al. |
| 6,263,249 B1 | 7/2001 | Stewart et al. |
| 6,309,401 B1 | 10/2001 | Redko et al. |
| 6,553,264 B2 | 4/2003 | Redko et al. |
| 6,574,512 B1 | 6/2003 | Zhang et al. |
| 6,587,733 B1 * | 7/2003 | Cross et al. ............ 607/116 |
| 6,639,153 B2 | 10/2003 | Hauge |
| 2001/0029395 A1 | 10/2001 | Stewart et al. |
| 2002/0072737 A1 | 6/2002 | Belden et al. |
| 2002/0117326 A1 | 8/2002 | Hauge |
| 2002/0128700 A1 | 9/2002 | Cross, Jr. |
| 2002/0147484 A1 | 10/2002 | Dahl et al. |
| 2002/0147487 A1 | 10/2002 | Sundquist et al. |
| 2003/0036787 A1 | 2/2003 | Redko et al. |

FOREIGN PATENT DOCUMENTS

| | | |
|---|---|---|
| WO | WO 00/11762 | 3/2000 |
| WO | WO 02/072192 | 9/2002 |

OTHER PUBLICATIONS

Brochure, "Pisces Quad Implant Manual, Model 3487A Lead Kit", *Medtronic, Inc.*, (1996).

* cited by examiner

METHOD OF USE OF IMPLANTABLE PERCUTANEOUS STIMULATION LEAD

RELATED APPLICATION

This application is a continuation of U.S. application Ser. No. 09/957,217, filed Sep. 20, 2001, now U.S. Pat. No. 7,072,719. U.S. application Ser. No. 09/957,217, filed Sep. 20, 2001, is incorporated herein by reference in its entirety.

FIELD OF THE INVENTION (This invention relates to a medical device and more particularly to a neurological stimulation lead that can be implanted in a human body.

BACKGROUND OF THE INVENTION

The medical device industry produces a wide variety of electronic and mechanical devices such as neurological stimulators, therapeutic substance infusion pumps, pacemakers, and defibrillators for treating patient medical conditions such as pain, movement disorders, functional disorders, spasticity, cancer, and cardiac disorders. Medical devices can be configured to be surgically implanted or connected externally to the patient receiving treatment and can be used either alone or in combination with pharmaceutical therapies and surgery to treat patient medical conditions. For certain medical conditions, medical devices provide the best and sometimes the only therapy to restore an individual to a more healthful condition and a fuller life. One type of medical device is an implantable neurological stimulation system typically includes a neurostimulator, an electrical stimulation lead, and an extension such as shown in Medtronic, Inc. brochure "Implantable Neurostimulation System" (1998). An implantable neurological stimulation system delivers electrical pulses to tissue such as neurological tissue or muscle to treat a medical condition.

Electrical stimulation leads can be configured as surgical leads that require an incision for implantation and as percutaneous leads that are implanted through a needle or introducer. Surgical leads are typically less constrained in their shape because the incision used for implantation can be easily varied according to the surgical lead shape. Percutaneous leads are typically constrained in their shape because of the requirement to be inserted through a needle or introducer. Implantation of percutaneous leads is shown in Medtronic, Inc. brochure Medtronic Percutaneous Implant Guide. It is difficult to implant a percutaneous lead in close combination with another percutaneous lead because it is difficult to coordinate the mechanical relationship between more than one percutaneous lead. It is also difficult to accommodate multiple lead bodies within a needle or introducer.

BRIEF SUMMARY OF THE INVENTION

An implantable neurological stimulation lead with interlocking elements has at least one first detail on the first lead body distal end that is configured to engage at least one second detail on the second lead body distal end that is complimentary to the first detail to mechanically couple the first lead body to the second lead body. The first lead body has an outer body, a first distal end, and a first proximal end. The first lead body has at least one electrode carried on the first distal end, at least one electrical connector carried on the first proximal end, at least one conductor electrically connecting the at least one electrode to the at least one connector carried in the lead body and electrically insulated by the lead body, and at least one detail on the first distal end outer body. The second lead body has an outer body, a second distal end, and a second proximal end. The second lead body has at least one electrode carried on the second distal end, at least one electrical connector carried on the second proximal end, at least one conductor electrically connecting the at least one electrode to the at least one connector carried in the lead body, and at least one second detail on the second distal end outer body. Many embodiments of the implantable neurological stimulation lead with interlocking elements and its methods of operation are possible.

DETAILED DESCRIPTION OF THE INVENTION

Figure 1:
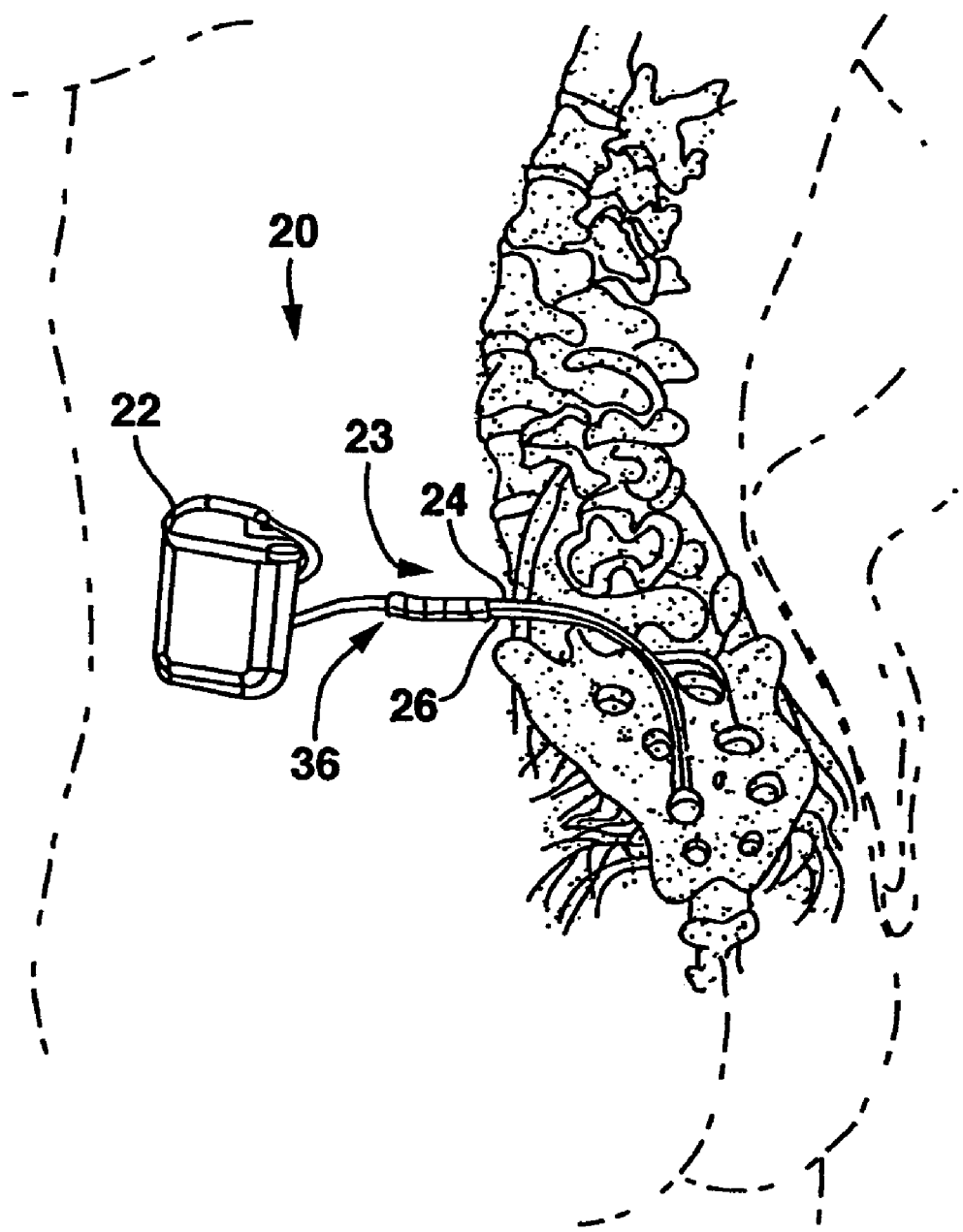
FIG. 1 shows a neurological stimulation system environment embodiment.
Figure 2:
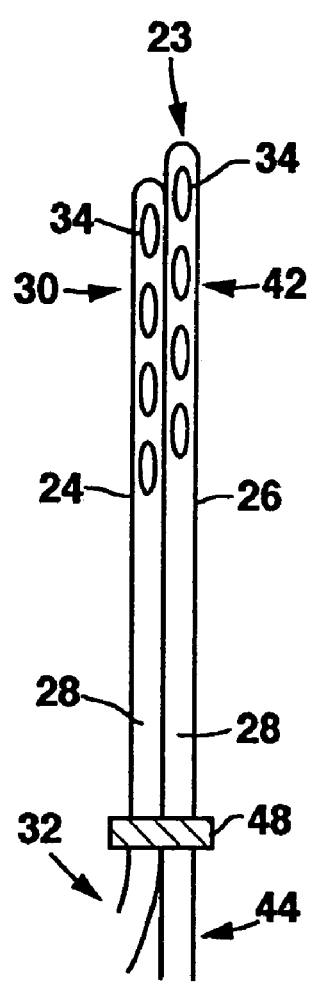
FIG. 2 shows a two lead embodiment.
Figure 3:
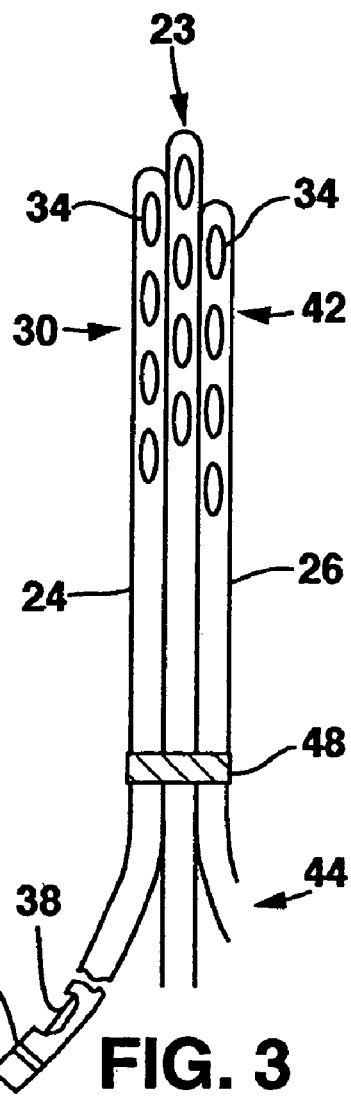
FIG. 3 shows a three lead embodiment.
Figure 4:
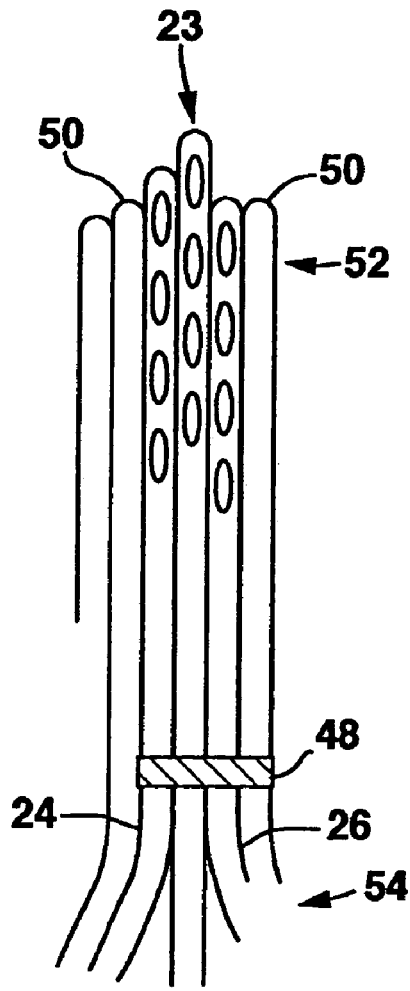
FIG. 4 shows a three lead and spacer embodiment.
Figure 5:
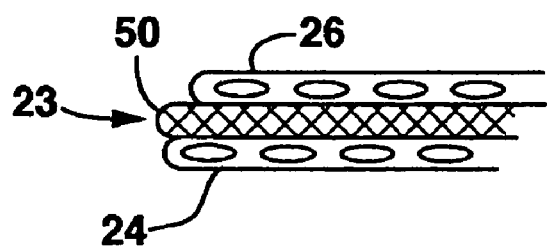
FIG. 5 shows a two lead and spacer embodiment.
Figure 6A:
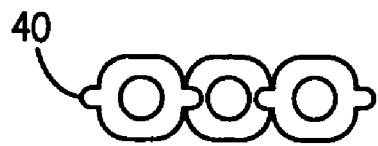
FIGS. 6a-6c show a coupling detail embodiments.
Figure 6B:
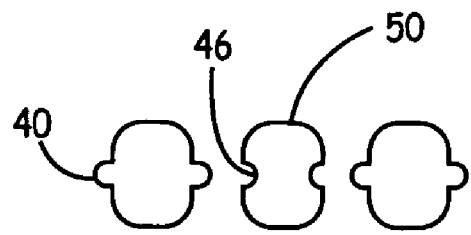
Figure 6C:
Figures 7A, 7B:
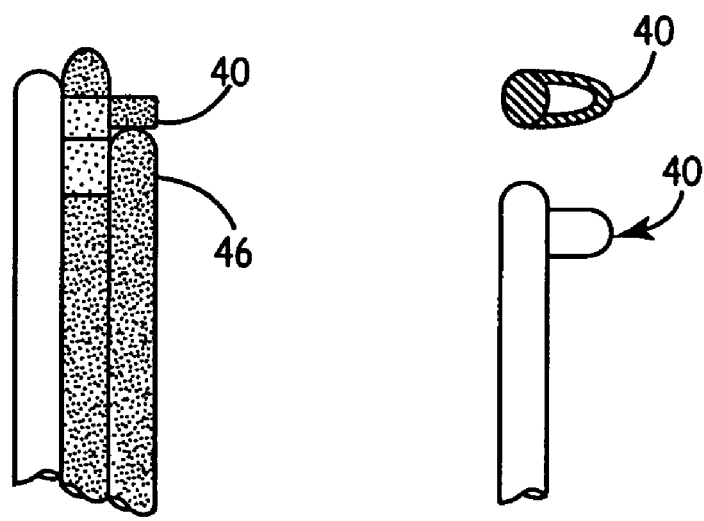
FIGS. 7a-7b show more coupling detail embodiments; and,
FIG. 8 shows a flow cart for a method.

FIG. 1 shows an environment of an implantable neurological stimulation system 20. The implantable neurological stimulation system 20 comprises an implantable neurological stimulator 22, a stimulation lead with interlocking elements 23, a first lead body 24, and a second lead body 26. The implantable neurological stimulator 22 provides a programmable stimulation signal that is delivered to a desired location or target to stimulate selected nerves or muscle tissue. The implantable neurological stimulator 22 is typically implanted in a subcutaneous pocket around the upper buttocks sometime after the stimulation lead has been implanted and its effectiveness verified.

FIGS. 2-5 show various implantable percutaneous stimulation lead with interlocking elements 23 embodiments. An implantable neurological stimulation lead with interlocking elements 23 comprises a first lead body 24 and a second lead body 26. These embodiments permit implantation of paddle or surgical style lead using percutaneous methods typically without the use of a large needle or introducer. These embodiments also allow the mechanical adjustment of electrodes in more than one percutaneous lead in relation to one another both axially and laterally.

The first lead body 24 has an outer body 28, a first distal end 30, and a first proximal end 32, at least one electrode 34, at least one electrical connector 36, at least one conductor 38, and at least one first detail 40 (FIGS. 6a-7b). The outer body 28 is manufactured from a material that is biocompatible and electrically insulating. The electrode 34 is carried on the first distal end 30. The electrode 34 can be configured as a ring or any portion of a ring to include a substantially flat electrode. The electrical connector 36 is carried on the first proximal end 32. The conductor 38 electrically connects the electrode 34 to the connector 36 and is insulated by the outer body 28. The first detail 40 is carried on the first distal end 30 outer body 28. The first lead body 24 is axially adjustable in relation to the second lead body 26.

The second lead body 26 has a outer body 28, a second distal end 42, and a second proximal end 44, at least one electrode 34, at least one electrical connector 36, at least one conductor 38, and at least one second detail 46. The outer body 28 is manufactured from a material that is biocompatible and electrically insulating. The electrode 34 is carried on the second distal end 42. The electrode 34 can be configured as a ring or any portion of a ring to include a substantially flat electrode 34. The electrical connector 36 is carried on the second proximal end 44. The conductor 38 electrically connects the electrode 34 to the connector 36 and is insulated by the outer body 28. The second detail 46 is carried on the second distal end 42 outer body 28. In addition to the first lead body 24 and the second lead body 26, there can be a third lead body, a forth lead body and so on.

The first detail 40 and the second detail 46 can be a wide variety of complimentary geometries that can be axially engaged and adjustable to mechanically couple the first lead body first distal end 30 to the second lead body second distal end 42. The first detail 40 and second detail 46 can extend the entire length of the first lead body 24 and second lead body 26 or any portion thereof provided at least one portion includes an area near the first lead body first distal end 30 and the second lead body second distal end 42. The first detail 40 on the first distal end 30 outer body 28 serves as a first means for connecting on the first distal end 30 outer body 28. The first detail 40 is complimentary to the second detail 46 and configured to engage each other to mechanically couple the first lead body first distal end 30 to the second lead body second distal end 42. The first detail 40 also serves as a first means for connecting and the second detail 46 serves as a second means for connecting to mechanically couple the first lead body first distal end 30 to the second lead body second distal end 42. Some embodiments can include an anchoring band 48 placed proximal to the electrode 34 to secure the first lead body 24 to the second lead body 26. Some embodiments can include at least one spacer body 50 having a spacer distal end 52 and a spacer proximal end 54. The spacer body 50 has at least one first spacer detail that is complimentary to the first detail 40 and at least one second spacer detail that is complimentary to the second detail 46. The spacer body 50 can be used to adjust lateral spacing between the electrodes 34 carried on the first 24 and second lead bodies 26 through varying the width or the spacer body 50 or by using multiple spacer bodies 50 in combination. Additionally, the spacer body 50 can be used to assist in anchoring the first lead body 24 and second lead body 26.

FIGS. 6a-7b shows various details and complimentary details embodiment. The various details can be a wide variety of complimentary geometries that can be axially engageable and adjustable to mechanically couple the first lead body distal end 30 to the second lead body distal end 42. For example, the first detail 40 can be a rail and the second detail 46 is a complimentary groove, and the first detail 40 can be a loop and the second detail 46 is the second lead body second distal end 42 that is engaged by the loop.

Figure 8:
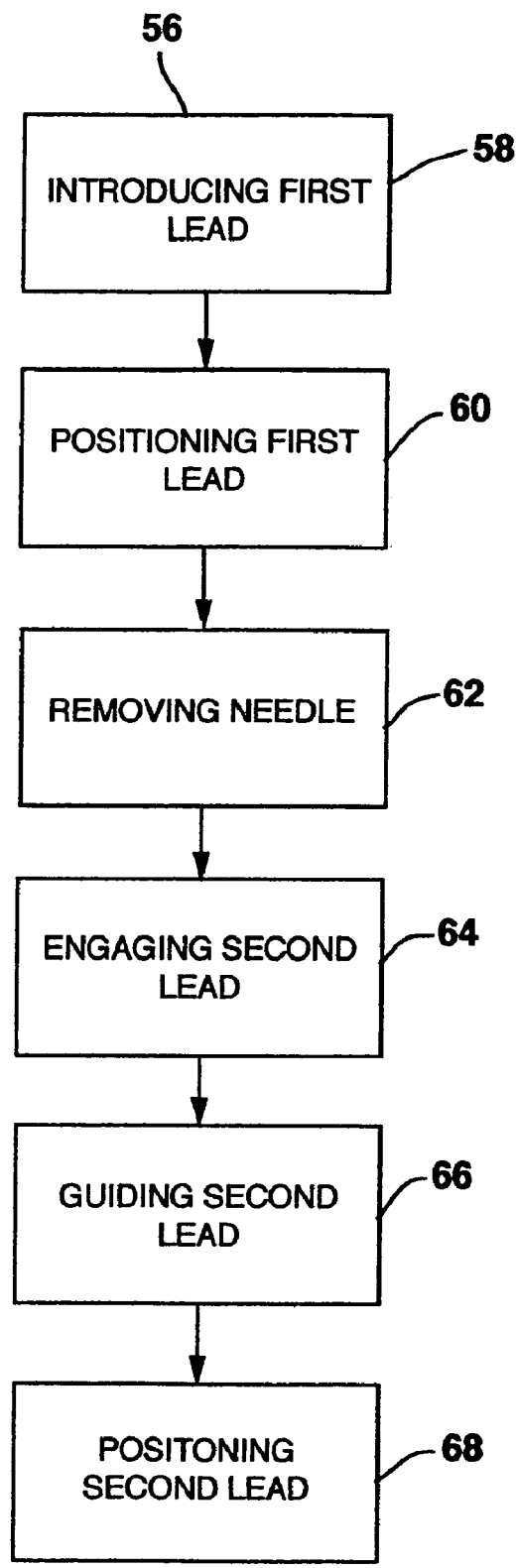

FIG. 8 shows a method embodiment for implanting the neurological stimulation lead with interlocking elements 56. A method for interconnecting two or more implantable percutaneous neurological stimulation leads comprises introducing a first lead body 58 having a first detail through a needle or introducer. Positioning the first lead body 60 at a first predetermined position. Removing the needle 62 while maintaining the first lead body at substantially the predetermined position. Engaging a second lead body 64 second detail into the first lead body first detail. Guiding the second lead body 66 using the first lead body as a guide. Positioning the second lead body 68 at a second predetermined position in relation to the first lead body. The method can also include adding one more spacers in a similar fashion to the first lead body and second lead body.

Figure 9A:
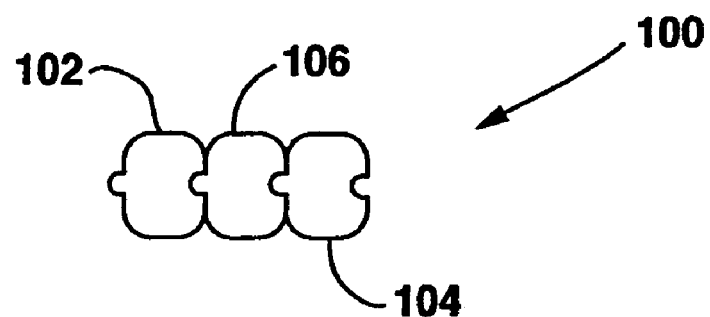
FIGS. 9a-c illustrates aspects of yet another an exemplary embodiment
Figure 9B:
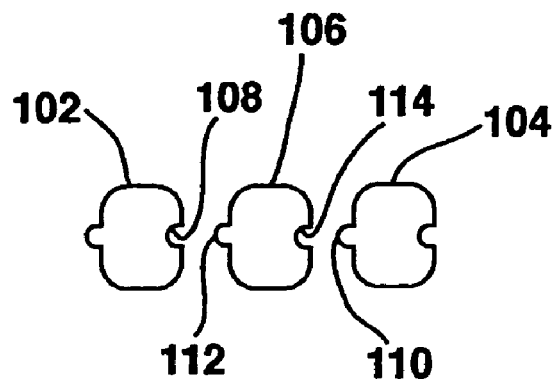
Figure 9C:
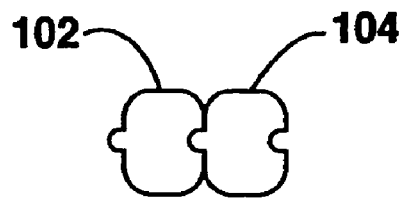

FIGS. 9a and 9b illustrate an implantable neurological stimulation lead 100 with interlocking elements. The lead 100 a first lead body 102, a second lead body 104, and a spacer body 106. The first lead body 102 includes at least one first detail, such as a groove 108, on the distal end of the first lead body 102. The second lead body 104 includes at least one second detail, such as a rail 110, on the distal end of the second lead body 104 that is complimentary to the first detail 108 on the first lead body 102. FIGS. 9a and 9b illustrate at least one first spacer detail (e.g., rail 112) that is complimentary to the first detail 108 and at least one second spacer detail (e.g., groove 114) that is complimentary to the second detail. FIGS. 9b and 9c illustrate the first detail 108 on the first lead body 102 as being configured to engage the at least one second detail 110 on the second lead body 104 to mechanically couple the distal end of the first lead body 102 to the distal end of the second lead body 104.

Thus, embodiments of the implantable neurological stimulation lead with interlocking elements are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method of interconnecting two or more implantable percutaneous neurological stimulation leads, the method comprising:
   introducing a first lead body having a first detail through a needle or introducer;
   positioning the first lead body at a first predetermined position;
   removing the needle or introducer while maintaining the first lead body at substantially the predetermined position;
   engaging a second lead body second detail into the first lead body first detail;
   guiding the second lead body using the first lead body as a guide; and
   positioning the second lead body at a second predetermined position in relation to the first lead body.

2. A method of interconnecting two or more implantable percutaneous neurological stimulation leads, the method comprising:
   introducing a first lead body through a needle or introducer, the first lead body having a first interlocking feature;
   positioning the first lead body at a first position;
   removing the needle or introducer while maintaining the first lead body at substantially the first position;
   engaging a second interlocking feature of a second lead body into the first interlocking feature of the first lead body, the first and second interlocking features being complementary to each other;
   guiding the second lead body using the first lead body as a guide; and
   positioning the second lead body at a second position in relation to the first lead body.

3. The method of claim 2 wherein the first interlocking feature comprises a groove and the second interlocking feature comprises a rail, the step of engaging a second interlocking feature of a second lead body second into the first interlocking feature of the first lead body including:

inserting the rail of the second lead body into the groove of the first lead body.

* * * * *